United States Patent
Hopermann et al.

(10) Patent No.: US 7,886,231 B2
(45) Date of Patent: Feb. 8, 2011

(54) SYSTEM FOR CONTROLLING AND MONITORING THERAPY MODULES OF A MEDICAL WORKSTATION

(75) Inventors: Hermann Hopermann, Badendorf (DE); Volker Schierschke, Lübeck (DE); Thomas Krüger, Reinfeld (DE)

(73) Assignee: Dräger Medical GmbH, Lübeck (DE)

( * ) Notice: Subject to any disclaimer, the term of this patent is extended or adjusted under 35 U.S.C. 154(b) by 796 days.

(21) Appl. No.: 11/867,239

(22) Filed: Oct. 4, 2007

(65) Prior Publication Data

US 2008/0086691 A1    Apr. 10, 2008

(30) Foreign Application Priority Data

Oct. 10, 2006    (DE)    ........................ 10 2006 047 770

(51) Int. Cl.
G06F 15/177    (2006.01)
G06F 3/00    (2006.01)
A61N 1/00    (2006.01)

(52) U.S. Cl. ............................. 715/736; 715/741; 607/2

(58) Field of Classification Search ................. 715/710, 715/810, 771, 772, 736, 741–744; 600/424, 600/459; 607/2
See application file for complete search history.

(56) References Cited

U.S. PATENT DOCUMENTS

2003/0060859 A1 *  3/2003  Bourget ........................ 607/60
2005/0267541 A1 *  12/2005  Scheiner et al. ............... 607/17

FOREIGN PATENT DOCUMENTS

WO    WO 2005/050523    6/2005
WO    WO 2005/050524    6/2005

* cited by examiner

*Primary Examiner*—Weilun Lo
*Assistant Examiner*—Truc T Chuong
(74) *Attorney, Agent, or Firm*—McGlew and Tuttle, P.C.

(57) ABSTRACT

A system is provided for controlling and monitoring therapy modules of a medical workstation. The system includes a first control and display unit, at least another control and display unit and at least one therapy module, which is either a ventilation module or an infusion module. The control and display units and the therapy module or therapy modules are connected to one another via bidirectional communications connections. The control and display units have a settable first display area for alarm and status reports of the therapy module or therapy modules and a second area for the display and modification of therapy settings of the therapy module or therapy modules. The communication between the control and display units is such that the display of the alarm and status reports for the therapy module or therapy modules can be turned off on one of the control and display units only if the display of the alarm and status reports of the therapy module or therapy modules is turned on, on at least one of the other control and display units and/or the communication between the control and display units is such that the display and modification of therapy settings of the therapy module or therapy modules can be turned off only if the display and modification is turned on, on at least one of the other said control and display units.

18 Claims, 1 Drawing Sheet

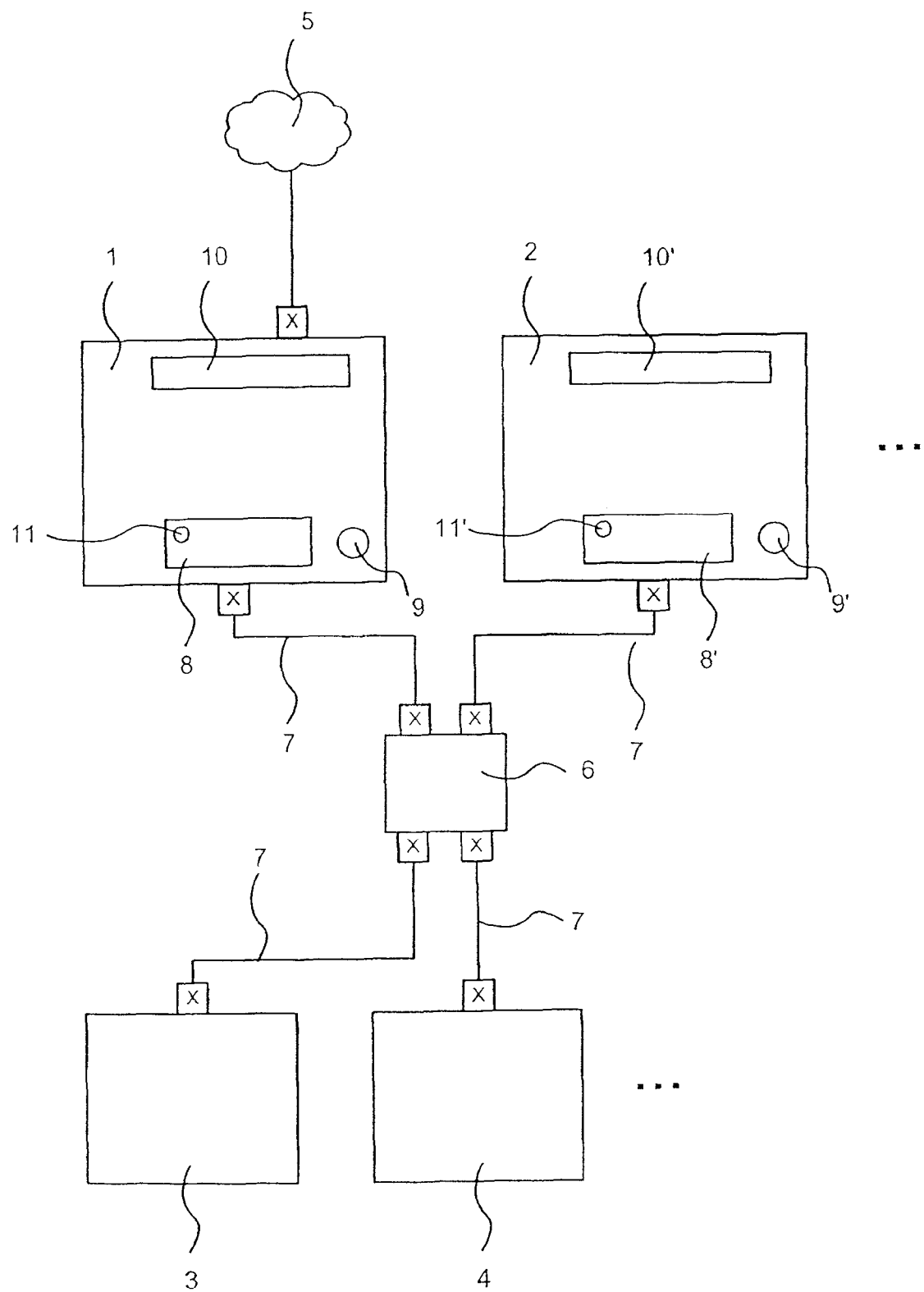

# US 7,886,231 B2

SYSTEM FOR CONTROLLING AND MONITORING THERAPY MODULES OF A MEDICAL WORKSTATION

CROSS REFERENCE TO RELATED APPLICATIONS

This application claims the benefit of priority under 35 U.S.C. §119 of German Patent Application DE 10 2006 047 770.7 filed Oct. 10, 2006, the entire contents of which are incorporated herein by reference.

FIELD OF THE INVENTION

The present invention pertains to a system for controlling and monitoring therapy modules of a medical workstation.

BACKGROUND OF THE INVENTION

Patient monitors, which detect, display and monitor various physiological parameters of the patient, are used in medical intensive care units in hospitals. These parameters include, for example, the electrocardiogram, invasively and noninvasively measured blood pressures, body temperatures, the oxygen saturation of the blood and the carbon dioxide concentration in the breathing gas.

The patient monitors used up to now have a control and display unit, among other things, for the graphic or numeric display of the measured parameters and for displaying alarms. In addition, the user has the possibility of configuring the patient monitor via the control and display unit, for example, in respect to the alarm limits, the layout of the display screen and parameter settings.

In many hospitals, the patient monitors are connected to one another via a network, so that the transmission of data to a PC or to a patient monitor located at another site in the hospital is possible. The prior-art patient monitors offer the possibility of displaying parameters and alarms, acknowledging or muting alarms and of changing configurations via another patient monitor or via a PC. Besides patient monitors which process only physiological parameters of the patient and can therefore be called passive devices, active medical workstations, which assume therapy functions, are used as well, depending on the clinical picture.

Such active therapy devices or therapy modules are, for example, respirators (also known as ventilators), hereinafter called ventilation modules for short, and syringe and infusion pumps, hereinafter called infusion modules for short.

Infusion pumps supply the patient with drugs, food or other solutions via an intravenous access and usually have an integrated control and display unit of their own.

Respirators support the patient's spontaneous breathing when needed or replace it entirely. These devices also have a control and display unit of their own, which is arranged on one side of the patient's bed. There are therapy modules for which remote control is available, so that the activation/deactivation of selected clinical routine functions such as alarm muting is also possible from the second side of the bed facing away from the device. This enables the user to optimize work procedures at the bedside.

Besides patient monitors and therapy modules, a patient data management system (PDMS), hereinafter called patient data system for short, is usually used in clinical intensive care units.

This is a program with functions, for example, therapy planning and therapy documentation, care planning and care documentation, detection and management of physician's reports, findings, laboratory data, diagnoses, ventilation data, vital data, and characteristics for the treatment. The patient data system runs, in general, on a separate computer, typically on a PC.

The computer for the patient data system is connected to a network. Devices that can be connected to a separate network for patient monitors besides the network for the patient data system are commercially available. These devices combine the function of the control and display unit of a patient monitor with access to a patient data system. The combination of the control and display unit of a therapy module with a patient data system is not known. The large number of patient monitors, therapy modules, computers for patient data systems that are used in an intensive care unit are connected to a corresponding number of control and display units. These cause costs, must be positioned at the bedside and usually have different control concepts. The latter leads to a considerable effort for training the users and increases the probability of operating errors.

The central operation of a system comprising modules for patient monitoring, ventilation, infusion and anesthesia is described in the patent applications WO 0020050523 and WO 00200505024.

SUMMARY OF THE INVENTION

The object of the present invention is to provide an improved system for controlling and monitoring therapy modules of a medical workstation with the possibility of simultaneously controlling different therapy modules in one system with a plurality of control and display units.

According to the invention, a system is provided for controlling and monitoring therapy modules of a medical workstation. The system includes a first control and display unit, at least another control and display unit and at least one therapy module, which is either a ventilation module or an infusion module. The control and display units and the therapy module or therapy modules are connected to one another via bidirectional communications connections. The control and display units have a settable first display area for alarm and status reports of the therapy module or therapy modules and a second area for the display and modification of therapy settings of the therapy module or therapy modules. The communication between the control and display units is such that the display of the alarm and status reports for the therapy module or therapy modules can be turned off on one of the control and display units only if the display of the alarm and status reports of the therapy module or therapy modules is turned on, on at least one of the other control and display units and/or the communication between the control and display units is such that the display and modification of therapy settings of the therapy module or therapy modules can be turned off only if the display and modification is turned on, on at least one of the other of the control and display units.

At least one of the control and display units may have access, via a network, to a patient data system, which can be displayed and controlled via the control and display unit.

At least one control and display unit may be integrated in the therapy module.

The control and display units and the therapy module or therapy modules may be connected to a central network element via Y-shaped communications connections.

The alarm and status reports of the ventilation module may pertain especially to one or more of the following variables or states: the airway pressure, the minute volume, the oxygen content, the respiration rate, apnea, the $CO_2$ content and/or the modes of respiration. The alarm and status reports of the infusion module may pertain especially to the end of the infusion, the current status of the infusion pump, the pressure, an air alarm and/or the transport flow.

The therapy settings for the ventilation module may comprise one or more of the following variables or parameters: the tidal volume, the respiration rate, the inspiration pressure, the positive end-expiratory pressure (PEEP), the inspiration time, the oxygen dispensing and/or trigger settings. The therapy settings for the infusion module may comprise the type of the syringe, the drug being dispensed, the infusion volume, the delivery rate, the duration of rise of the delivery rate, the duration of decrease of the delivery rate, and/or the bolus rate.

The communication between the control and display units may be designed such that in case of failure of one of the control and display units, the alarm and status reports as well as therapy settings of the therapy module that were hitherto available on the failed control and display unit only are automatically displayed on the other control and display unit, especially associated with an alarm of the other control and display unit.

The system may advantageously be designed such that it is possible to change therapy settings of a therapy module on any of the control and display units that displays therapy settings.

The communication between the control and display units and the design of the functionalities may be program-controlled.

An element acting as a setter may be contained in the area for modifying therapy settings, so that all visible elements for the same parameter are deactivated on the other control and display unit or control and display units for the user with the selection of the element on one of the control and display units. Other elements may also be deactivated on the other control and display unit or control and display units besides the selected element. The other elements may be functionally dependent on the selected element or pertain to the same therapy.

Unlimited control of therapy modules is possible with the system according to the invention, especially from both sides of the bed with the consequence of optimal support of work processes in the intensive care unit. The ability of the entire system to be controlled is fully preserved in case of failure of a control and display unit, and consistency is ensured for the user at any time in changing therapy settings via a plurality of control and display units.

The control and display units can be set in respect to the type and the scope of the display of alarm and status reports and/or in respect to the type and the scope of the display and modification of therapy settings of the therapy module or therapy modules.

An exemplary embodiment will be explained below on the basis of the only FIGURE, which shows the basic elements of a system for controlling and monitoring a plurality of therapy modules of a medical workstation. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a schematic view of the system according to the invention.

DESCRIPTION OF THE PREFERRED EMBODIMENT

Referring to the drawings in particular, the system shown has a first control and display unit 1 and at least one second control and display unit 2 as well as at least one or especially two therapy modules, as shown, namely, a ventilation module 3 and an infusion module 4.

The control and display units 1, 2 and the therapy modules 3, 4 are connected via bidirectional communications connections 7, especially in a Y connection via a central network element 6.

The control and display units 1, 2 have a first display area 10, 10' for alarm and status reports of the therapy modules 3, 4, which said display area can be set in terms of the type and the scope of the display, and a second area 8, 8' for the display and modification of therapy settings of the therapy modules 3, 4. The communication between the control and display units 1, 2 is designed, especially in a program-controlled manner providing an alarm and status program and a display and modification of therapy settings program, in such a way that the display of the alarm and status reports for the therapy modules 3, 4 on one of the control and display units 1 or 2 and/or the display and modification of therapy settings of the therapy modules 3, 4 can be turned off only if the display of the alarm and status reports of the therapy modules 3, 4 and/or the display and modification of therapy settings on the second control and display unit 1 or 2 is turned on.

At least the first control and display unit 1 has access, via a network 5, to a patient data system with patient- and therapy-relevant data and processing programs.

In case of failure of one of the control and display units 1 or 2, the alarm and status reports as well as settings of the therapy module 3, 4, which were only available in the system on the control and display unit 1 or 2 that failed, are automatically set for display on the other control and display unit 1 or 2 of the system.

The failure of the control and display unit 1 or 2 triggers an alarm on the other control and display unit 1 or 2 in a program-controlled manner.

It is possible to change the therapy settings of a therapy module 3, 4 on all control and display units 1, 2, on which the therapy settings of the therapy module 3, 4 are set for display.

The therapy settings are changed in the following steps:

1. Selection of the element 11 or 11', hereinafter called "setter," for the parameter in question in the area 8, 8';

2. selection of the new value; and 3. acknowledgment and thus activation of the new value.

The selected setter (element 11 or 11') is optically marked on the control and display unit 1, 2 on which the selection was performed.

With the selection of the setter (element 11 or 11') on one of the control and display units 1, 2, all visible setters for the same parameter are deactivated for the user on the other control and display units 1, 2, i.e., they can no longer be selected for modification. Besides the selected setter, other setters can be deactivated as well. These are preferably setters which depend on the selected setter, for example, the respiration rate, the inspiration time and the expiration time depend on each other in "respiration" therapy. Or these are setters for the same therapy.

Deactivated setters are either marked optically on the control and display units 1, 2 or the user receives an instruction when the user attempts to operate a deactivated setter. The value that was valid before the selection is displayed in the deactivated setters.

A control button 9, 9' is preferably located at each control and display unit 1, 2 for changing a set value. This control button 9, 9' preferably offers a function with which the modified value can be acknowledged by pushing the button.

After acknowledging the modified value, the selection of the selected setter goes out, and the new value is taken over by the therapy module 3, 4. At the same time, deactivated setters on other control and display units are again activated for the user and thus they become available for selection.

With the acknowledgment of the modified value, this value becomes visible on all control and display units of the system if the setters for the corresponding therapy module 3, 4 were set for display on the particular display and control unit.

Each control and display unit 1, 2 has a processor and an interface for connection to the bidirectional communications connections 7 preferably of a communications network. The communications network is preferably designed in a Y pattern by means of a central network element 6. The programs on the processors of the control and display units 1, 2 are designed such that via the bidirectional communications connections 7, they exchange data that pertain to the current status of the therapy modules 3, 4 as well as to the current status of the control and display units 1, 2 that is visible for the user.

While a specific embodiment of the invention has been shown and described in detail to illustrate the application of the principles of the invention, it will be understood that the invention may be embodied otherwise without departing from such principles.

What is claimed is:

1. A system for controlling and monitoring one or more therapy modules of a medical workstation, the system comprising:
    a first control and display unit;
    a second control and display unit;
    a therapy module comprising either a ventilation module or an infusion module;
    bidirectional communications connections, said first control and display unit and said second control and display unit and said therapy module being connected to one another via said bidirectional communications connections, each of said first control and display unit and said second control and display unit including a settable first display area for alarm and status reports of said therapy module and a second area for the display and modification of therapy settings of said therapy module, wherein:
    communication between said first control and display unit and said second control and display unit is such that the display of the alarm and status reports for said therapy module can be turned off on one of said first control and display unit and said second control and display unit only if the display of the alarm and status reports of said therapy module is turned on at least one of the other said first control and display unit and said second control and display unit;
    communication between said first control and display unit and said second control and display unit is such that the display and modification of therapy settings of said therapy module can be turned off on one of said first control and display unit and said second control and display unit only if the display and modification is turned on, on the other of said first control and display unit and said second control and display unit;
    at least one of said first control and display unit and said second control and display unit has access, via said network, to a patient data system, which can be displayed and controlled via said first control and display unit or said second control and display unit;
    said bidirectional communications connections comprise a central network element and medical network communications connections, wherein said first control and display unit and said second control and display unit and said therapy modules are connected to said central network element via said medical network communications connections.

2. A system in accordance with claim 1, further comprising a network connection to a network, wherein at least one of said first control and display unit and said second control and display unit has access, via said network, to a patient data system, which can be displayed and controlled via said first control and display unit or said second control and display unit.

3. A system in accordance with claim 1, wherein at least one of said first control and display unit and said second control and display unit is integrated in said therapy module.

4. A system in accordance with claim 1, wherein said bidirectional communications connections comprise a central network element and said medical network communications connections wherein said first control and display unit and said second control and display unit and said therapy module are connected to said central network element via said medical network communications connections.

5. A system in accordance with claim 1, wherein the alarm and status reports of said ventilation module pertain to one or more of the following variables or states: an airway pressure, a minute volume, an oxygen content, a respiration rate, apnea, a $CO_2$ content and/or the modes of respiration.

6. A system in accordance with claim 1, wherein the alarm and status reports of said infusion module pertain to at least one of an end of an infusion, a current status of an infusion pump, pressure, an air alarm and/or transport flow.

7. A system in accordance with claim 1, wherein the therapy settings for said ventilation module comprise at least one of the following variables or parameters comprising: a tidal volume, a respiration rate, an inspiration pressure, a positive end-expiratory pressure (PEEP), inspiration time, an oxygen dispensing and/or trigger settings.

8. A system in accordance with claim 1, wherein the therapy settings for said infusion module comprise at least one of a type of syringe, a drug being dispensed, an infusion volume, a delivery rate, a duration of rise of the delivery rate, a duration of decrease of the delivery rate, and/or a bolus rate.

9. A system in accordance with claim 1, wherein the communication between said first control and display unit and said second control and display unit is, in case of failure of a control and display unit, the alarm and status reports as well as therapy settings of said therapy module that were hitherto available on said failed control and display unit automatically displayed on said other control and display unit associated with an alarm of said other control and display unit.

10. A system in accordance with claim 1, wherein said first control and display unit and said second control and display unit provides for a change of therapy settings of said therapy module on any said first control and display unit and said second control and display unit that displays therapy settings.

11. A system in accordance with claim 1, wherein communication between said first control and display unit and said second control and display unit and a design of functionalities thereof is program-controlled.

12. A system in accordance with claim 1, wherein an element acting as a setter is contained in said area for modifying therapy settings, so that all visible elements for the same parameter are deactivated on said other control and display unit or control and display units for the user with the selection of said element on one of said control and display units.

13. A system in accordance with claim 12, wherein other elements are also deactivated on said other control and display unit or control and display units, besides said selected element.

14. A system in accordance with claim 13, wherein the other elements are functionally dependent on said selected element or pertain to the same therapy.

15. A system for controlling and monitoring therapy modules of a medical workstation, the system comprising:
- a plurality of therapy modules, each therapy module comprising either a ventilation module or an infusion module;
- bidirectional communications connections;
- a first control and display unit including a first unit settable alarm and status display area for alarm and status reports of one or more of said therapy modules and a first unit settings area for the display and modification of therapy settings of one or more of said therapy modules;
- a second control and display unit including a second unit settable alarm and status display area for alarm and status reports of one or more of said therapy modules and a second unit settings area for the display and modification of therapy settings of one or more of said therapy modules, said first control and display unit and said second control and display unit and said therapy modules being connected to one another via said bidirectional communications connections;
- an alarm and status program, said first control and display unit and said second control and display unit communicating to provide said alarm and status program in which a display of the alarm and status for one of said therapy modules can be turned off on one of said first control and display unit and said second control and display unit only if the display of the alarm and status of said one of said therapy modules is turned on at the other said first control and display unit and said second control and display unit; and
- a display and modification of therapy settings program, said first control and display unit and said second control and display unit communicating to provide said display and modification of therapy settings program in which a display of display and modification of therapy settings of said one of said therapy modules can be turned off on one of said first control and display unit and said second control and display unit only if the display of said display and modification of therapy settings is turned on at the other of said first control and display unit and said second control and display unit;
- at least one of said first control and display unit and said second control and display unit has access, via said network, to a patient data system, which can be displayed and controlled via said first control and display unit or said second control and display unit;
- said bidirectional communications connections comprise a central network element and medical network communications connections, wherein said first control and display unit and said second control and display unit and said therapy modules are connected to said central network element via said medical network communications connections.

16. A system in accordance with claim 15, wherein at least one of said first control and display unit and said second control and display unit is integrated in said therapy module.

17. A system in accordance with claim 15, wherein:
- alarm and status reports of said ventilation module pertain to one or more of the following variables or states: an airway pressure, a minute volume, an oxygen content, a respiration rate, apnea, a $CO_2$ content and/or modes of respiration; and
- alarm and status reports of said infusion module pertain to at least one of an end of an infusion, a current status of an infusion pump, pressure, an air alarm and/or transport flow;
- therapy settings for said ventilation module comprise at least one of the following variables or parameters comprising: a tidal volume, a respiration rate, an inspiration pressure, a positive end-expiratory pressure (PEEP), inspiration time, an oxygen dispensing and/or trigger settings; and
- therapy settings for said infusion module comprise at least one of a type of syringe, a drug being dispensed, an infusion volume, a delivery rate, a duration of rise of the delivery rate, a duration of decrease of the delivery rate, and/or a bolus rate.

18. A system in accordance with claim 15, wherein in case of failure of a control and display unit, the alarm and status reports as well as therapy settings of said therapy module that were provided on the failed control and display unit is displayed on said other control and display unit associated with an alarm of said other control and display unit.

* * * * *